United States Patent [19]
Schultz

[11] Patent Number: 5,910,132
[45] Date of Patent: Jun. 8, 1999

[54] SAFETY IV CATHETER GUARD

[75] Inventor: Willard F. Schultz, Bethlehem, Pa.

[73] Assignee: B. Braun Medical Inc., Allentown, Pa.

[21] Appl. No.: 09/003,299

[22] Filed: Jan. 6, 1998

[51] Int. Cl.[6] .................................................... A61M 5/32
[52] U.S. Cl. ........................ 604/162; 604/263; 604/198
[58] Field of Search .................................. 604/110, 192, 604/198, 197, 263, 162

[56] References Cited

U.S. PATENT DOCUMENTS

| | | | |
|---|---|---|---|
| 4,747,831 | 5/1988 | Kulli ........................................ | 604/110 |
| 4,978,344 | 12/1990 | Dombrowski et al. ................. | 604/198 |
| 5,069,667 | 12/1991 | Freundlich et al. .................... | 604/110 |
| 5,183,468 | 2/1993 | McLees ................................... | 604/110 |
| 5,334,149 | 8/1994 | Nortman et al. ....................... | 604/110 |
| 5,348,544 | 9/1994 | Sweeney et al. ...................... | 604/198 |
| 5,423,766 | 6/1995 | Di Cesare .............................. | 604/198 |

*Primary Examiner*—Wynn Wood Coggins
*Assistant Examiner*—Sharon Finkel
*Attorney, Agent, or Firm*—Hopgood, Calimafde, Kalil & Judlowe, LLP

[57] ABSTRACT

A safety IV catheter includes an end cap or guard and a disc-shaped lock plate having an opening through which the needle passes. One end of an actuator member passes through a second off-center opening in the lock plate and its other end passes through a flange fitted about the needle hub. In the prepared or ready position of the catheter, the guard is mounted about the distal end of the needle hub. As the needle is retracted to the activated position, the needle tip is received within the needle guard and the lost motion of the actuator member is taken up by the engagement of the needle hub and the lower end of the actuator member. This, in turn, causes the lock plate to be canted or rocked at an angle about the distal end of the needle to grip and lock the needle tip within the needle guard and to prevent further axial movement of the needle.

17 Claims, 1 Drawing Sheet

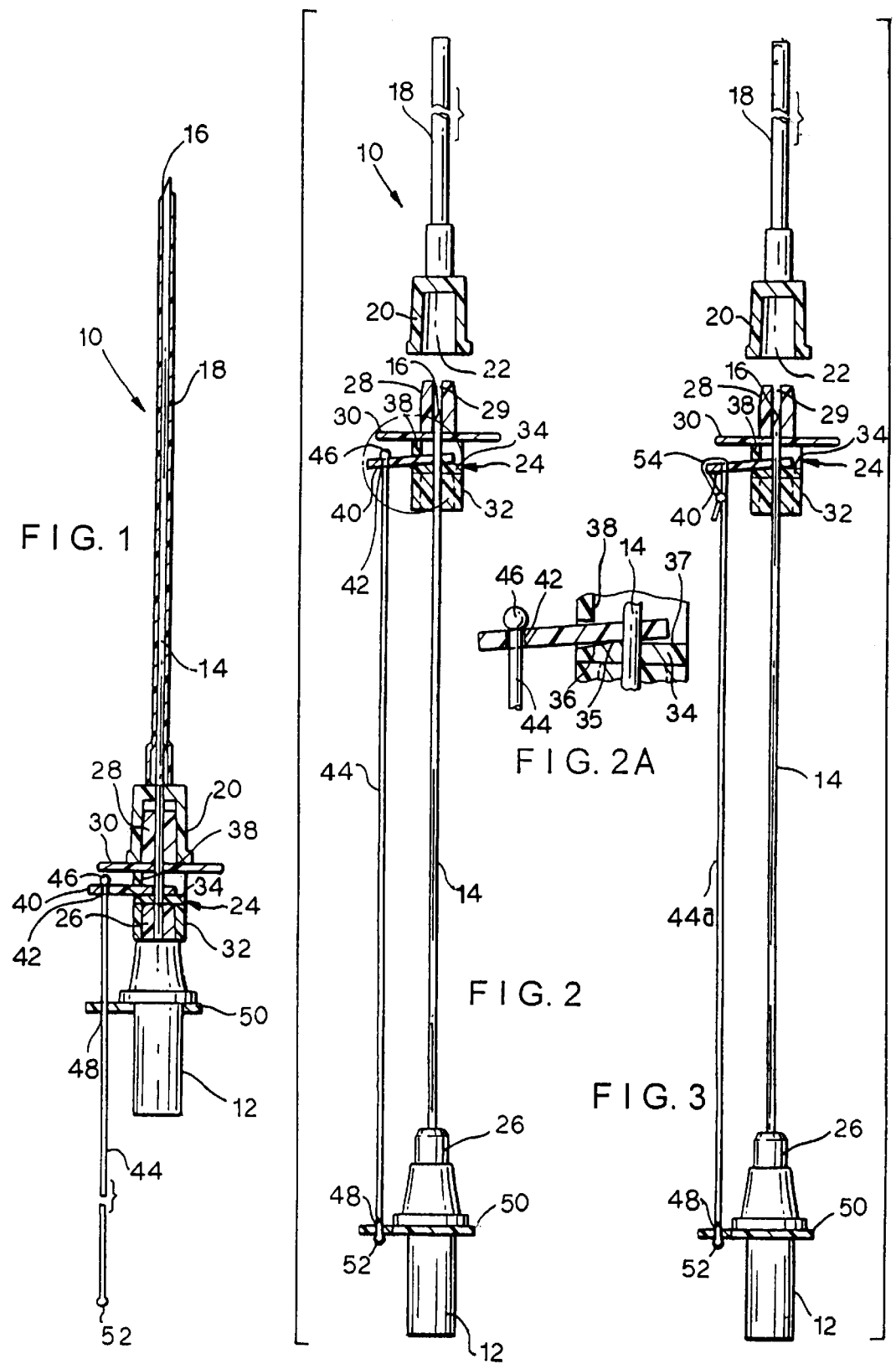

SAFETY IV CATHETER GUARD

TECHNICAL FIELD

This invention relates generally to intravenous (IV) catheters, and, in particular, to a safety IV catheter in which the needle tip is automatically covered and locked in a protected condition after needle withdrawal to prevent the health-care worker from making accidental contact with the needle tip.

BACKGROUND OF THE INVENTION

I.V. catheters are primarily used to administer fluids, sometimes containing medications, directly into a patient's vascular system. The catheter is inserted into a patient's vein by a health care worker by using a handheld placement device that includes a sharp tip needle. The needle is positioned in the interior hollow portion of the catheter with its tip extended slightly beyond the edge of the catheter. The end of the apparatus opposite the needle tip is made up of the needle connected to a needle hub which is capable of being held by the health care worker during the insertion procedure.

The insertion procedure contains four basic steps: (1) the health care worker inserts the needle and catheter together into the patient's vein; (2) after insertion into the vein with the needle point, the catheter is forwarded into the vein of the patient by the health care worker pushing the catheter with his or her finger; (3) the health care worker withdraws the needle by grasping the hub end (opposite the point end) while at the same time applying pressure to the patient's skin at the insertion site with his or her free hand; and (4) the health care worker then tapes the now inserted catheter to the patient's skin and connects the exposed end of the catheter, the catheter hub, to the source of the fluid to be administered into the patient's vein.

The problem is that immediately after the withdrawal of the needle from the patient's vein, the health care worker who is, at this time involved in at least two urgent procedures must place the exposed needle tip at a nearby location and address the tasks required to accomplish the needle withdrawal. It is at this juncture that the exposed needle tip creates a danger of an accidental needle stick or scratch occurring, which leaves the health care worker vulnerable to the transmission of dangerous blood-borne pathogens, including AIDS and hepatitis.

This danger to the health care worker from accidental needle sticks has caused an impetus for the development of a safer IV catheter in which the occurrence of such accidental needle sticks is prevented. As a result, numerous different safety catheters have been developed to achieve this result, one of which is disclosed, for example, in Swedish Patent publication SE556318. In these safety IV catheters, upon the withdrawal of the needle from the patient, a protective member is automatically positioned over the exposed needle tip so that accidental contact with the needle tip is prevented.

Among the problems that have been encountered in the use of currently available safety IV catheters is that the protective guard that is positioned over the needle tip after needle removal may itself be moved away from its protective position so that the needle tip is no longer shielded by the needle guard. This may occur, for example, when a force is inadvertently applied to the needle guard, to overcome the retentive force that had previously maintained the protective guard over the needle tip. Other problems associated with the known safety catheter is their relative complexity, high cost, and difficulty of fabrication.

SUMMARY OF THE INVENTION

It is accordingly an object of the present invention to provide a safety IV catheter which reliably and automatically prevents accidental contact with the needle tip after use.

It is a further object of the invention to provide a safety IV catheter in which removal of the needle guard from the needle after needle withdrawal is effectively prevented even when a force is applied to the needle.

It is another object of the present invention to provide a safety IV catheter of the type described which is relatively simple and inexpensive to fabricate.

To these ends, the safety IV catheter of the invention includes an end cap or guard and a disc-shaped lock plate having an opening through which the needle passes. An upper end of a actuator member passes through a second off-center opening in the lock plate and its other, lower end passes through an opening in a flange of the needle hub. In the prepared or ready position of the catheter, one end of the needle guard is received within the catheter hub and its other end is mounted about the distal end of the needle hub. As the needle is retracted to the activated position, the tip of the needle is received within the needle guard, and the lost motion of the actuator member is taken up by the engagement of the needle hub flange with the lower end of the actuator member. The axial force now exerted by the actuator member on the lock plate causes the latter to cant or rock about the needle shaft so that it firmly engages and grips the needle, thereby to securely retain the needle tip in the needle guard and prevent axial movement of the needle. Further movement of the needle hub increases the locking force exerted by the lock plate on the needle tip.

To the accomplishment of the above and to such further objects as may hereinafter appear, the present invention relates to a safety IV catheter as defined in the appended claims, and as described in the following specification as considered with the accompanying drawings, in which:

BRIEF DESCRIPTION OF THE DRAWINGS

FIG. 1 is a side elevation, partly in cross-section, of a safety IV catheter in accordance with one embodiment of the invention in the ready position;

FIG. 2 is a side elevation, partly in cross-section, of the safety IV catheter of FIG. 1 in the activated position;

FIG. 2A is an enlarged view of a portion of the catheter of FIGS. 1 and 2; and

FIG. 3 is a side elevation of a safety IV catheter in accordance with a modification of the invention shown in the activated position.

DESCRIPTION OF THE PREFERRED EMBODIMENTS

The safety IV catheter of the invention, generally designated 10, as in the embodiment illustrated in FIGS. 1 and 2, includes a needle hub 12 which securely receives the proximal end of a needle 14 having a sharpened tip 16. As is conventional, the needle 14 is received within a hollow tubular catheter 18, the proximal end of which is concentrically affixed within the distal end of a catheter hub 20. The catheter hub 20 terminates at its proximal end in a luer fitting 22 adapted to receive a tubing set, which, in a known manner, administers intravenous fluid into the patient.

In use, the distal tip of the needle 14 and the catheter 18 are inserted into a patient's vein. Thereafter, the health care practitioner manually places the catheter 18 further into the vein and then withdraws the needle 14 by grasping and moving by hand the proximal end of the needle hub 12. The luer 22 of the catheter hub 20 is then fitted with a source of the fluid that is to be administered into the patient's vein. In accordance with the present invention, as the needle 14 is completely withdrawn from the patient, the bare tip 16 of the needle is automatically and securely locked within a needle guard so that accidental contact with the needle tip is prevented.

To this end, as shown in FIG. 1, the safety IV catheter of the invention includes a needle guard 24, the proximal end of which is releasably seated over the frusto-conical distal end 26 of the needle hub 12 when the catheter 18 is in the ready position shown in FIG. 1. The distal end 28 of the needle guard 24 is split at 29 to allow the guard to fit snugly into the luer end of the catheter hub 20 and to be readily released when the catheter hub 20 is pulled away. A flange 30 extends about the lower proximal end of split end 29. The needle guard includes a lower depending portion 32 that extends downwardly from flange 30. An internal shelf 34 in portion 32 includes, as seen best in FIG. 2A, an axially offset fulcrum or pivot point 35 formed at the junction of a tapered surface 36 and a level upper surface 37. Axially offset projection 38 is formed at the upper end of portion 32, and a lock plate 40 is positioned between the upper surface of shelf 34 and the lower end of projection 38.

Split end 28, flange 30, shelf 34, and lock plate 40 each include an axially aligned opening through which the needle 14 freely passes when the catheter is in the ready position. Lock plate 40 also includes an off-axis opening 42 through which the upper end of an actuator member 44 passes. In the embodiment of FIGS. 1 and 2, a bead 46 having a diameter greater than that of opening 42 is formed at the upper end of actuator member 44 to prevent it from passing through opening 42. The lower end of actuator member 44 passes through an opening 48 in a flange 50 affixed to the periphery of needle hub 12. A bead 52 having a diameter greater than that of opening 48 is affixed to the lower end of actuator member 44 to prevent it from passing through the opening. Member 44 may be, as in the embodiment of FIG. 1, in the form of an elongated rod preferably made of a material such as a high-density polyethylene that allows it to flex or spring slightly.

In use, after the catheter 18 is inserted into the patient's blood vessel, the catheter hub is held in place with a finger of one hand, and needle hub 12 is grasped by the thumb and forefinger of the other hand to withdraw the needle from the patient and also to separate the needle hub 12 from the lower end of the needle guard 28. As the needle hub 12 is retracted, relative lost motion is effected between the needle hub 12 and the actuator member 44 until the needle tip 16 is received within the split end 29 of the needle guard 24, as seen in FIG. 2. At about this time, also as shown in FIG. 2, the flange 50 on needle hub 12 engages the bead 52 at the lower end of actuator member 44, thereby to take up the lost motion of the actuator member 44. This causes the lock plate 40 to cant or rock about fulcrum 35 and the needle shaft in a counterclockwise direction, as viewed in FIG. 2, so that the lock plate 40 securely grips and binds the needle shaft to prevent further axial motion of the needle whose tip is now completely enclosed within the split end 29 of the needle guard 24.

Continued motion of the needle hub 12 away from the catheter hub 20 releases the needle guard 24 and needle hub 20 from the catheter hub 20. As the needle 14 is pulled further away from catheter 18, the actuator member 44 in combination with the lock plate 40 exert a force on the needle guard 24 to pull the needle guard out of the lower end of the catheter hub 20.

In the event an upward axial force is thereafter inadvertently applied to the needle guard 24, the locking force exerted by the lock plate 40 on the needle shaft, preventing movement of the needle tip away from the needle guard 24, is increased. Moreover, if an inadvertent downward force is thereafter applied to the needle guard 24, the internal projection 38 is moved into engagement with the lock plate 40 so as to exert a downward force on the lock plate 40 that maintains it in its canted or locking position on the needle shaft.

The embodiment of the invention illustrated in FIG. 3 is the same as that illustrated in FIGS. 1 and 2 except that the actuator member 44a is in the form of a thin wire having a knot 54 at its upper end, which passes through an opening 42 in lock plate 40. Knot 50 secures the upper end of the wire actuator member to the lock plate 40, and prevents the upper end of the wire actuator member from passing downward through the opening in the lock plate 40.

It will be appreciated that the safety IV catheter of the invention provides reliable protection against inadvertent contact with a needle tip after catheter insertion, even when an axial force is subsequently applied to the needle guard. It will also be understood that the safety catheter of the invention may be fabricated easily and at a relatively low cost by the use of current fabricating processes. It will be additionally understood that whereas the present invention has been described hereinabove with respect to several preferred embodiments, modifications to those embodiments may be made, such as the use of a fish line or other strong but flexible material as the actuator member, without necessarily departing from the spirit and scope of the invention.

What is claimed is:

1. A catheter comprising a needle, a needle hub affixed to one end of said needle, a catheter hub, a needle guard intermediate and releasably secured to said needle hub and said catheter hub, said needle guard comprising locking means having an opening for freely receiving the shaft of said needle when said catheter is in a ready condition, said needle hub being movable axially away from said needle guard to an activated position in which the tip of said needle is received within said needle guard, and actuating means in engagement with said locking means, said needle hub including means for operatively engaging said actuating means when said needle hub is moved to its activated position, thereby to cause said actuating means to move said locking means to a locking position in which it contacts the shaft of said needle at said opening, thereby to restrict further axial movement of said needle, said actuating means including lost motion means extending between said locking means and said needle hub and capable of relative displacement with respect to said needle hub as the latter is moved toward its said activated position, said lost motion means comprising an actuator having an upper end engaging said needle guard when the latter is in its ready position, said locking means further including a lock plate having a second opening radially spaced from said first opening for receiving the upper end of said actuator.

2. The catheter of claim 1, in which said needle guard includes a split distal end adapted to be snugly but releasably placed in the luer opening of said catheter hub.

3. The catheter of claim 1, in which said needle guard includes a projection positioned to exert a force on said lock plate to retain said lock plate means in locking engagement with the needle shaft when a force is applied to said needle guard.

4. The catheter of claim 3, in which said needle hub includes a peripheral flange for engaging the lower end of said actuator when said needle hub is in its said retracted activated position.

5. The catheter of claim 4, in which said actuator comprises a at each of its ends for respectively engaging its upper end to said needle guard and for engaging said needle hub when the latter is moved to its retracted activated position.

6. The catheter of claim 3, in which said needle hub includes a peripheral flange for engaging the lower end of said actuating means when said needle hub is in its said retracted activated position.

7. The catheter of claim 4, in which said actuating means comprises means bead at each of its ends for respectively engaging its upper end to said needle guard and for engaging said needle hub when the latter is moved to its retracted activated position.

8. The catheter of claim 1, in which said needle guard includes a split distal end adapted to be snugly but releasably placed in the luer opening of said catheter hub.

9. The catheter of claim 8, in which said needle guard includes a projection positioned to exert a force on said locking means to retain said locking means in locking engagement with the needle shaft when a force is applied to said needle guard.

10. The catheter of claim 9, in which said needle hub includes a peripheral flange for engaging the lower end of said actuator when said needle hub is in its said retracted activated position.

11. The catheter of claim 10, in which said actuator comprises means at each of its ends for respectively engaging its upper end to said needle guard and for engaging said needle hub when the latter is moved to its retracted activated position.

12. The catheter of claim 1, in which said needle guard includes a projection positioned to exert a force on said locking means to retain said locking means in locking engagement with the needle shaft when a force is applied to said needle guard.

13. The catheter of claim 12, in which said needle hub includes a peripheral flange for engaging the lower end of said actuator when said needle hub is in its said retracted activated position.

14. The catheter of claim 1, in which said needle guard includes a member providing an offset fulcrum, said locking means being pivotable about said fulcrum to its said locking position.

15. A catheter comprising a needle, a needle hub affixed to one end of said needle, a catheter hub, a needle guard intermediate and releasably secured to said needle hub and said catheter hub, said needle guard comprising locking means having an opening for freely receiving the shaft of said needle when said catheter is in a ready condition, said needle hub being movable axially away from said needle guard to an activated position in which the tip of said needle is received within said needle guard, and actuating means in engagement with said locking means, said needle hub including means for operatively engaging said actuating means when said needle hub is moved to its activated position, thereby to cause said actuating means to move said locking means to a locking position in which it contacts the shaft of said needle at said opening, thereby to restrict further axial movement of said needle, said actuating means comprising an upper end engaging said needle guard when the latter is in its said ready position, said locking means including a lock plate having a second opening radially spaced from said first opening for receiving the upper end of said actuating means.

16. The catheter of claim 15, in which said needle guard includes a projection positioned to exert a force on said locking means to retain said locking means in locking engagement with the needle shaft when a force is applied to said needle guard.

17. The catheter of claim 16, in which said needle guard includes a member providing an offset fulcrum, said locking means being pivotable about said fulcrum to its said locking position.

* * * * *